US010357512B2

(12) United States Patent
Chtourou

(10) Patent No.: US 10,357,512 B2
(45) Date of Patent: Jul. 23, 2019

(54) METHOD FOR PREPARING UNIVERSAL PLASMA

(71) Applicant: LABORATOIRE FRANCAIS DU FRACTIONNEMENT ET DES BIOTECHNOLOGIES, Les Ulis (FR)

(72) Inventor: Abdessatar Chtourou, Elancourt (FR)

(73) Assignee: LABORATOIRE FRANCAIS DU FRACTIONNEMENT ET DES BIOTECHNOLOGIES, Les Ulis (FR)

(*) Notice: Subject to any disclaimer, the term of this patent is extended or adjusted under 35 U.S.C. 154(b) by 0 days.

(21) Appl. No.: 15/512,185

(22) PCT Filed: Oct. 9, 2015

(86) PCT No.: PCT/EP2015/073471
§ 371 (c)(1),
(2) Date: Mar. 17, 2017

(87) PCT Pub. No.: WO2016/055647
PCT Pub. Date: Apr. 14, 2016

(65) Prior Publication Data
US 2017/0281679 A1    Oct. 5, 2017

(30) Foreign Application Priority Data
Oct. 9, 2014  (FR) .................................. 14 59679

(51) Int. Cl.
| A61K 35/16 | (2015.01) |
| A61K 9/19 | (2006.01) |
| B01D 15/38 | (2006.01) |
| A61K 9/00 | (2006.01) |
| A61K 9/08 | (2006.01) |
| B01D 61/14 | (2006.01) |

(52) U.S. Cl.
CPC ............ *A61K 35/16* (2013.01); *A61K 9/0019* (2013.01); *A61K 9/08* (2013.01); *A61K 9/19* (2013.01); *B01D 15/3809* (2013.01); *B01D 61/145* (2013.01); *B01D 2311/2626* (2013.01)

(58) Field of Classification Search
CPC ........ A61K 35/16; A61K 9/0019; A61K 9/08; A61K 9/19; B01D 15/3809; B01D 61/145; B01D 2311/2626
See application file for complete search history.

(56) References Cited

U.S. PATENT DOCUMENTS

| 2004/0242857 A1 | 12/2004 | Nilsson |
| 2009/0074749 A1 | 3/2009 | Chtourou et al. |
| 2011/0008459 A1 | 1/2011 | Marguerre et al. |
| 2013/0143198 A1* | 6/2013 | Sailliol ............... A01N 1/0284 435/2 |

FOREIGN PATENT DOCUMENTS

| CN | 101346153 A | 1/2009 |
| EP | 0 572 194 A1 | 12/1993 |
| EP | 1 775 000 A2 | 4/2007 |
| EP | 2 556 848 A1 | 2/2013 |
| FR | 3 008 097 A1 | 1/2015 |
| FR | 3 008 098 A1 | 1/2015 |
| WO | WO 01/27623 A2 | 4/2001 |
| WO | WO 2007/077365 A2 | 7/2007 |
| WO | WO 2012/022914 A1 | 2/2012 |
| WO | WO 2013/066251 A1 | 5/2013 |

OTHER PUBLICATIONS

Solheim B.G. et al., "Indications for use and cost-effectiveness of pathogen-reduced ABO-universal plasma", Current Opinion in Hematology, 2008, vol. 15, pp. 612-617. (Year: 2008).*
Judd et al., "Isohemagglutinin-depleted solvent detergent plasma: A universal viral-inactivated plasma for patients of any ABO blood type," Blood, vol. 94, No. 10, Suppl. 1 Part 1, p. 375a, Nov. 1999.
Anonymous, "Octaplasma™," retrieved from the Internet: http://www.octopharma.ca/fileadmin/user_upload/octoapharma.ca/20120502_PM_950_Octoplasma.pdf, Jul. 25, 2012.
Noddeland et al., "Universal solvent/detergent-treated fresh frozen plasma (Uniplas)-rationale and clinical properties," Thrombosis Research, vol. 107, pp. S33-S37, Oct. 2002.
Taiwan Search Report issued in application No. 104133370 dated Jan. 23, 2017.
French Search Report issued in application No. FR 1459679 dated May 29, 2015.
International Search Report issued in application No. PCT/EP2015/073471.
Ness, "Transfusion Medicine: An Overview and Update," Clinical Chemistry, vol. 46, No. 8, pp. 1270-1276, 2000.

* cited by examiner

*Primary Examiner* — Satyendra K Singh
(74) *Attorney, Agent, or Firm* — Potomac Law Group, PLLC

(57) ABSTRACT

The present invention relates to an universal plasma, originating from a mixture of plasmas originating from donor individuals of blood groups A, B, AB and/or O and compatible with all the blood groups and the preparation process thereof.

11 Claims, 5 Drawing Sheets

METHOD FOR PREPARING UNIVERSAL PLASMA

TECHNICAL FIELD

The present invention relates to a universal plasma made virally safe, poor in anti-A and anti-B antibodies, and compatible with all the blood groups, as well as the preparation process thereof.

TECHNOLOGICAL BACKGROUND

"Blood plasma" or "plasma" is the liquid component of blood, in which the blood cells are in suspension. It is possible to separate plasma from whole blood by centrifugation or filtration across a membrane. Blood plasma is constituted essentially by water, plasma proteins (mainly albumin and antibodies) and coagulation factors, including fibrinogen. Blood plasma is used in therapy for treating serious coagulopathies with collapse of all the coagulation factors and also for treating acute haemorrhages, with overall deficiency of the coagulation factors.

Currently, the therapeutic plasma generally used is fresh frozen plasma (FFP) originating from biologically qualified donations (immunohaematological tests, nucleic acid amplification detection of HIV, HCV and HBV viruses), which can be made safe vis-à-vis pathogens by quarantine or physico-chemical treatment. Such a plasma needs to be stored at a temperature less than or equal to −25° C., which means that it can only be administered after thawing under specific conditions. Furthermore, this type of plasma cannot be stored for more than a year, which leads to significant losses. Finally, this therapeutic plasma must be used with care since its administration must comply with the rules regarding delivery based on recipient ABO compatibilities. In addition to the use of compatible plasmas, iso-group plasma transfusion must therefore be preferred in order to avoid any risk of post-transfusion haemolysis due to ABO incompatibility.

Because of the restrictions linked to its use and to its storage and therefore its availability, such fresh frozen plasma proves unsuited to use under emergency conditions, in particular in a hospital environment or in a location outside a hospital environment (scenes of accidents or disasters, areas that are difficult to access, areas with restricted or non-existent access to cold chains, theatres of military operation).

A need therefore exists for a plasma corresponding to the constraints of the hospital and non-hospital environment, can be stored at ambient temperature, free of any form of bacterial, viral or parasitic contamination and compatible with any recipient, independently of their ABO blood group.

Application WO2012/022914 describes a process for obtaining a lyophilized plasma, originating from a mixture of plasma from selected donors and belonging exclusively to blood group AB or to blood groups A or B. The process described in application WO2012/022914 cannot be implemented with donors belonging to blood group O.

Application US20110008459 describes a universal plasma obtained by mixing the plasmas from donors of blood groups A and B and optionally AB to the exclusion of any plasma originating from donors of blood group O, in which the free anti-A and anti-B antibody titre is less than 16 for immunoglobulins M (IgM) and less than 64 for immunoglobulins G (IgG).

SUMMARY OF THE INVENTION

The inventors have developed a process for the preparation of an universal plasma the characteristics of which meet storage and use requirements that have not yet been met, irrespective of the blood group to which this plasma belongs.

Thus the invention relates to a process for the preparation of an universal plasma, comprising the following steps:
a) Mixing non-universal unit plasma obtained from a sample of donors,
b) Removing the anti-A and anti-B antibodies present in the plasma by immunoaffinity chromatography, or by in batch depletion and
c) Optionally, the lyophilization or atomization of the universal plasma originating from step b).

The process of the invention finally makes it possible to obtain an "universal plasma" that can be administered to any patient whatever the blood group and without determining the patient's blood group beforehand. The universal plasma according to the invention meets the regulatory requirements to which the plasmas currently used in therapy are subject, in particular the concentrations of coagulation factors are satisfactory (for example the concentration of factor VIII is greater than or equal to 0.5 IU/mL, the concentration of factor V is greater than or equal to 0.7 IU/mL, the concentration of factor XI is greater than or equal to 2 g/L) and there is no coagulation factors activation.

In a particular embodiment, step b) is carried out by means of immunoaffinity chromatography or by in Batch depletion on a support, the matrix of which is grafted with oligosaccharide groups antigenically similar to blood groups A and/or B, for example according to the techniques described in application WO2007/077365 or using a matrix as described in applications FR 13 56635 or FR 13 56636.

In a particular embodiment, said donors belong to the blood group selected from blood group A, blood group B, blood group AB and/or blood group O.

In a particular embodiment, the process for the preparation of a universal plasma can further comprise a step of lyophilization, cryodessiccation or atomization at the end of step b), making it possible to obtain a "lyophilized universal plasma", a "cryodesiccated universal plasma", or an "atomized universal plasma" by means of an appropriate lyophilization, cryodessiccation or atomization step.

In a particular embodiment, the universal plasma originating from step b) has an anti-A antibody content and/or an anti-B antibody content in the universal plasma in accordance with a negative result at a 1/64 dilution in the Coombs test, carried out according to method 2.6.20 of the European Pharmacopoeia 07/2011:20620.

In a particular embodiment, the process for the preparation of an universal plasma can further comprise a biological safety step, by means of viral inactivation and/or ultrafiltration upstream of step a).

The present invention also relates to a universal plasma, preferably a universal plasma in which the anti-A antibody content and the anti-B antibody content is in accordance with a negative result in the Coombs test at a 1/64 dilution in the Coombs test, carried out according to method 2.6.20 of the European Pharmacopoeia 07/2011:20620.

The present invention also relates to the use of such an universal plasma for the treatment of patients:
- suffering from severe haemorrhages, in particular of traumatic origin, replacing multiple coagulation factors, in emergency situations when a concentrate of coagulation factors is not available,
- suffering from traumatic or spontaneous haemorraghes under oral anticoagulant (OAC),
- suffering from severe vitamin K deficiency, or
- suffering from thrombotic thrombocytopaenic purpura.

DETAILED DESCRIPTION

Other characteristics and advantages of the present invention will become apparent on reading the following detailed description and preferred embodiment of the invention, given by way of example.

By "non-universal unit plasma", is meant plasma collected from a single human donor individual, irrespective of their blood group. This unit plasma can be prepared from whole blood or be collected by aphaeresis. This non-universal unit plasma is a human plasma. Preferentially, within the context of this invention, the non-universal unit plasmas constituting the mixture of plasmas of step a) of the process of the invention are collected by aphaeresis. Preferentially, the non-universal unit plasmas constituting the mixture of plasmas of step a) correspond to the same regulatory requirements governing the plasmas currently used in therapy or for fractionation. They therefore meet current requirements, in particular in terms of haemostasis factor levels. The donor individuals must therefore meet the regulatory criteria for plasma donation eligibility. Preferentially, the non-universal unit plasmas are obtained from male donors or donors free of anti-HLA antibodies. Moreover, in the context of the present invention, the donors must have a normal haemostasis balance characterized by a factor VIII level at least equal to 0.9 IU/mL.

By "human donor individual", is meant a human individual capable of giving (free or paid) blood or blood components.

By "mixture of plasmas" or "pool of plasmas", is meant a mixture of non-universal unit human plasmas. In the context of the invention, the "pool of plasmas" can be a pool of therapeutic plasmas, that can be used directly in therapy or a pool of plasmas for fractionation. According to the invention, the pool of plasmas is advantageously leucodepleted in order to make the plasma safe from risks of transmission of prions or of other infectious agents. Advantageously, the leucodepleted plasma according to the invention has a limited residual leucocyte content ≤$1.0 \times 10^6$/litre. Preferentially, a "mixture of plasmas" or "pool of plasmas" corresponds to a mixture of at least 2 non-universal unit human plasmas, preferentially of at least 5 non-universal unit human plasmas, even more preferentially of at least 10 non-universal unit human plasmas.

In a particular embodiment of the invention, a "mixture of plasmas" or "pool of plasmas" corresponds to a mixture of at least 100 different non-universal unit human plasmas. In another particular embodiment of the invention, a "mixture of plasmas" or "pool of plasmas" corresponds to a mixture of at least 1500 different non-universal unit human plasmas.

In a particular embodiment of the invention, a "mixture of plasmas" or "pool of plasmas" corresponds to a mixture of at least 2,000 different non-universal unit human plasmas. In another particular embodiment of the invention, a "mixture of plasmas" or "pool of plasmas" corresponds to a mixture of at least 10,000 different non-universal unit human plasmas.

In another particular embodiment of the invention, the number of non-universal unit plasmas used in order to constitute a "mixture of plasmas" or "pool of plasmas" is advantageously adjusted in order to guarantee biological safety. Thus, the addition of additional biological safety steps makes it possible to increase the number of non-universal unit plasmas while minimizing the biological risk.

By "whole blood", is meant all of the compounds and cells constituting the blood.

By "aphaeresis", is meant a technique for collecting certain blood components from a donor. The components that it is desired to collect are separated by centrifugation and stored, whilst the components not collected are reinjected into the donor.

In a particular embodiment, the mixture of plasmas from step a) of the process according to the invention is obtained from the non-universal unit plasmas from at least 2 different donors, at least 5 different donors, preferentially from at least 10 different human donor individuals. In a particular embodiment, the mixture of non-universal unit plasmas of step a) of the process according to the invention is obtained from 100 different human donor individuals.

In another particular embodiment, the mixture of non-universal unit plasmas of step a) of the process according to the invention is obtained from 1,500 different human donor individuals.

Such a limitation in terms of the number of human donor individuals makes it possible to considerably reduce the residual infectious risk while benefiting from the advantages of the mixture: reduced immunogenicity, beneficial effect on the infectious risk due to the dilution or the neutralization of the pathogenic agents, and obtaining an universal plasma for blood grouping. It also allows simplified traceability of the donor individuals.

In another particular embodiment, the mixture of non-universal unit plasmas of step a) of the process according to the invention is obtained from at least 2,000 human donor individuals, preferentially from at least 5,000, even more preferentially from at least 10,000 different human donor individuals. In order not to limit the number of human donor individuals, suitable additional measures can be put in place for characterizing and making safe the non-universal unit plasmas: separation of the donors at risk, quarantine, nucleic acid amplification detection of the genome of parvovirus B19 or of the hepatitis A, hepatitis B or HIV virus, detection of anti-hepatitis C antibodies, additional step of viral removal or inactivation, or any other suitable biological safety measure.

Preferentially, said human donor individuals belong to blood groups A, B, AB or O, which makes it possible not to exclude them from donor categories on the basis of their blood group, and therefore, to increase the volumes of source plasma that can be used according to the invention. By "human donor individual belonging to blood group A, B, AB or O", is meant a donor individual with the phenotype A, B, AB or O respectively. Belonging to a particular blood group has no influence on the process of the invention. No prior selection of the non-universal unit plasmas is carried out upstream of said process.

The applicant has surprisingly and unexpectedly found that the process according to the invention made it possible to obtain a universal plasma from non-universal unit plasmas, irrespective of the blood group to which the donor individuals belong. In other words, the process of the invention makes it possible to obtain a universal plasma from non-universal unit plasmas originating from a sample from donor individuals belonging to blood group A, B, AB or O. In a particular embodiment, the mixture of non-universal unit plasmas of step a) of the process according to the invention advantageously originate from donor individuals belonging to blood groups A, B, AB and O.

By "blood group", is meant a blood classification based on the presence or the absence of antigenic substances on the surface of the red blood cells. These antigenic substances define the ABO system. The A antigen corresponds to the presence of an N-acetyl-galactosamine grafted in position $\alpha_{1-3}$ of the epitope (H chain). The B antigen corresponds to the presence of a galactose grafted in position $\alpha_{1-3}$ of the epitope (H chain). The ABO system dictates the rules of blood transfusion compatibility. Failure to comply with these rules can lead to a haemolytic accident in the transfused individual. As the plasma contains antibodies depending on the group in the ABO system, the recipient's red blood cells should not have the corresponding antigens. Thus, a plasma comprising anti-A antibodies should not be administered to a patient belonging to blood group A, and vice versa.

By "anti-A antibody" or "anti-blood group A antibody", is meant any antibody recognizing the antigens of blood group A.

By "anti-B antibody" or "anti-blood group B antibody", is meant any antibody recognizing the antigens of blood group B.

In a particular embodiment of the invention, the anti-A antibodies and anti-B antibodies consist of immunoglobulins recognizing the antigens of blood group A and/or B, in particular immunoglobulins G or M.

In another particular embodiment of the invention, the anti-A antibodies and anti-B antibodies consist of immunoglobulins G or M recognizing the antigens of blood group A and/or B, in particular haemolysins or agglutinins. The anti-A and anti-B antibodies of haemolysin type are immunoglobulins G that can be present in the plasma and lead to the lysis of the red blood cells.

By "universal plasma", is meant a plasma that can be used for any recipient individual, independently of their blood group. The universal plasma advantageously makes it possible to avoid the constraint of ABO compatibility or ABO iso-group between the donor and recipient individuals. It is thus possible to produce and store only a single type of universal plasma, instead of the 4 types of plasma (A, B, AB and O) currently necessary in order to satisfy ABO compatibility. The universal plasma thus avoids wastage of out-of-date plasma due to incorrect predictions requirements dependent on the blood groups of the patients. Such a universal plasma advantageously makes it possible to reduce the space dedicated to storage of the plasma, and also removes the risks of accidental incompatible transfusion. The "universal plasma" consists in particular of a plasma poor in any antibody directed against the antigens of blood group A and/or of blood group B, in particular poor in anti-A antibodies and/or of anti-B antibodies.

Advantageously, the plasma obtained at the end of step b) of the process of the invention contains no anti-A or anti-B antibodies or contains a lower residual level of anti-A and/or anti-B antibodies in accordance with a negative result at a 1/64 dilution in the Coombs test and is described as "universal plasma".

In a particular embodiment of the invention, the universal plasma advantageously shows a negative result in the Coombs test at a 1/32 dilution, even more advantageously at a 1/16 dilution, even more advantageously at a 1/8 dilution or less.

By "Coombs test" is meant the direct or indirect Coombs test as described in paragraph 2.6.20 of the European Pharmacopoeia 01/2005:20620 or in chapter 2.6.20 of the European Pharmacopoeia 01/2008:20620 or of the European Pharmacopoeia 07/2011:20620. The indirect Coombs test consists of an indirect method using an antiglobulin as described for example in chapter 2.6.20 of the European Pharmacopoeia 01/2005:20620 or of the European Pharmacopoeia 07/2011:20620. The direct Coombs test consists of a direct haemagglutination method, using papain-treated cells, as a reference method for the detection of anti-A and anti-B antibodies using 3 standards (a positive control, a negative control and a limit test reference preparation) as described for example in chapter 2.6.20 of the European Pharmacopoeia 01/2008:20620 or of the European Pharmacopoeia 07/2011:20620.

Step b) of said process relates to the removal of the anti-A and anti-B antibodies present in the plasma by immunoaffinity chromatography or by in batch depletion. This step is essential in order to obtain an universal plasma that can be administered directly to the recipient irrespective of their ABO blood group.

The plasma originating from step a) is subjected to a immunoaffinity chromatography step or by in batch depletion on a support grafted with groups antigenically similar to blood groups A and/or B, preferably on a column filled with such a support. Preferably, the chromatographic or in batch depletion support is constituted by a polymer matrix onto which are grafted spacers or coupling arms, being grafted in turn with oligosaccharides advantageously representing trisaccharides corresponding to the epitopes of blood groups A and B.

By "in batch depletion", is meant a purification method by affinity by means of a support grafted with specific ligands, elution and washing fractions being separated from said support after incubation with molecules of interest by centrifugation to recover said support.

The immunoaffinity chromatography or in batch depletion matrix comprises polymer particles onto which at least one oligosaccharide corresponding to a blood group A and/or group B epitope is grafted, said oligosaccharide being grafted onto said particles via a spacer, characterized in that said spacer has the formula (I) —NH—$R_1$—CO—NH—$R_2$—, in which $R_1$ is a $C_4$-$C_6$ alkyl group, $R_2$ is a $C_3$-$C_8$ alkyl group, and said spacer is linked by its amine function to the polymer particle.

In a particular embodiment, the matrix comprises (i) polymer particles onto which at least one oligosaccharide corresponding to a blood group A epitope is grafted, and/or (ii) polymer particles onto which at least one oligosaccharide corresponding to a blood group B epitope is grafted. In a preferred embodiment, the matrix comprises (i) polymer particles onto which at least one oligosaccharide corresponding to a blood group A epitope is grafted, and (ii) polymer particles onto which at least one oligosaccharide corresponding to a blood group B epitope is grafted.

In another embodiment, the matrix comprises polymer particles onto which both at least one oligosaccharide corresponding to a blood group A epitope, and at least one oligosaccharide corresponding to a blood group B epitope, are grafted.

In a particular embodiment, the matrix comprises a mixture of (i) polymer particles onto which at least one oligosaccharide corresponding to a blood group A epitope is grafted, (ii) polymer particles onto which at least one oligosaccharide corresponding to a blood group B epitope is grafted, and (iii) polymer particles onto which both at least one oligosaccharide corresponding to a blood group A epitope, and at least one oligosaccharide corresponding to a blood group B epitope, are grafted.

In particular, very good results are obtained by utilizing such a support, the trisaccharides of which, corresponding to the blood group A epitope, have the structure N-acetylgalactosamine (GalNAc)-Galactose (Gal)-Fucose (Fuc), and those corresponding to the blood group B epitope have the structure Galactose-Galactose-Fucose (Gal-Gal-Fuc).

In a preferred embodiment, cross-linked cellulose beads onto which ligands which are trisaccharides corresponding to a blood group A epitope (N-acetylgalactosamine (GalNAc)-Galactose(Gal)- Fucose) are grafted, and cross-linked cellulose beads onto which ligands which are trisaccharides corresponding to a blood group B epitope (Galactose-Galactose-Fucose) are grafted, are mixed. The trisaccharides are grafted onto the beads by means of a spacer of formula: NH—$C_5H_{10}$—CO—NH—$C_3H_6$.

The support:

The matrix of the invention comprises a support based on polymer particles, and is preferably in the form of a gel or a resin.

These polymer particles are preferably spherical or oblong in shape, and may in particular be beads. These polymer particles generally have an average size of approximately 0.1 µm to approximately 1000 µm, preferably of approximately 20 to approximately 500 µm, yet more preferably of approximately 50 to approximately 200 µm, yet more preferably of approximately 70 µm to approximately 120 µm in diameter. Preferably these particles are porous.

The polymer can be natural or non-natural, organic or inorganic, cross-linked or not cross-linked The polymer is preferably an organic polymer, preferably cross-linked.

In a preferred embodiment, the polymer is cellulose, and the particles are preferably beads of porous cellulose. Further preferably, the cellulose is cross-linked.

Other types of possible polymers include agarose, dextran, polyacrylates, polystyrene, polyacrylamide, polymethacrylamide, copolymers of styrene and divinylbenzene, or mixtures of these polymers.

The ligands:

The ligands borne by the support according to the invention are oligosaccharides representing the antigens of blood groups A and/or B, which are naturally monosaccharides.

More precisely, the oligosaccharide corresponding to a blood group A epitope and/or the oligosaccharide corresponding to a blood group B epitope borne by the matrix according to the invention are typically trisaccharides. The term "oligosaccharides corresponding to a blood group epitope" refers to units that are antigenically identical or similar to the antigenic determinants recognized by the anti-A and anti-B antibodies respectively. The ligands borne by the support according to the invention are therefore specific to the anti-A or anti-B antibodies.

Preferably the oligosaccharide corresponding to a blood group A epitope, used as ligand in the invention, is an N-acetylgalactosamine (GalNAc)-Galactose(Gal)-Fucose trisaccharide, more precisely N-acetylGal$\alpha_{1-3}$(Fuc$\alpha_{1-2}$)Gal; the spacer is linked by means of the oxygen atom preferably linked to the carbon in position 1 of the galactose.

The oligosaccharide corresponding to a blood group B epitope, used as ligand in the invention, is preferably a Galactose-Galactose-Fucose oligosaccharide, more precisely Gal$\alpha_{1-3}$(Fuc$\alpha_{1-2}$)Gal; the spacer is linked by means of the oxygen atom preferably linked to the carbon in position 1 of the galactose. Advantageously, the density of ligands, i.e. the quantity of grafted ligands (namely of oligosaccharides corresponding to a blood group A or B epitope), per volume of matrix in the form of gel, can be comprised between approximately 0.2 and approximately 0.7 mg/ml of matrix, yet more preferably between approximately 0.3 and approximately 0.4 mg/ml of matrix. Preferably the density of oligosaccharides is approximately 0.3 mg/ml of matrix.

The spacer has the formula (I) —NH—$R_1$—CO—NH—$R_2$—, in which:

$R_1$ is a linear or branched $C_4$-$C_6$ alkyl group, $R_2$ is a linear or branched $C_3$-$C_8$ alkyl group said spacer being linked by its amine function (in bold above) to the polymer particle.

In a particular embodiment, $R_1$ represents a linear alkyl group, preferably, $R_1$ is a $C_5$ alkyl group and $R_2$ represents a linear alkyl group, preferably, $R_2$ is a $C_3$ alkyl group. A polymer particle can bear one or more spacers.

The spacer makes it possible to reduce the steric hindrance and to increase the accessibility of the ligand vis-à-vis anti-A and anti-B antibodies to be bound.

The spacer serves to immobilize, on a particle, either an oligosaccharide corresponding to a blood group A epitope, which is preferably an N-acetylGal$\alpha_{1-3}$(Fuc$\alpha_{1-2}$)Gal trisaccharide as described above, or an oligosaccharide corresponding to a blood group B epitope, which is preferably a Gal$\alpha_{1-3}$(Fuc$\alpha_{1-2}$)Gal trisaccharide as described above.

In a preferred embodiment, the ligands (preferably trisaccharides as described above) are grafted onto the polymer particles by means of a spacer of formula: NH—$C_5H_{10}$—CO—NH—$C_3H_6$.

Such a chromatographic or in batch depletion support very advantageously represents a gel or resin as described in the applications WO2007/077365, FR 13 56635 or FR 13 56636 or a commercially available gel or a resin such as GLYCOSORB® ABO (Glycorex Transplantation AS, Sweden), the affinity matrix Sepharose 4B grafted with trisaccharides of blood groups A and B (Dextra Laboratories Limited—United Kingdom), or any other equivalent matrix. This chromatographic or in batch depletion support allows the simultaneous removal of the anti-A and anti-B antibodies in a single step of immunoaffinity chromatography or in Batch depletion.

In a preferred embodiment, the polymer particles onto which at least one oligosaccharide corresponding to a blood group A epitope is grafted, and the polymer particles onto which at least one oligosaccharide corresponding to a blood group B epitope is grafted, can then be mixed, for example in a proportion of 25/75 to 75/25 (v/v), preferably approximately 50/50 (v/v). It is in fact possible to adjust the proportion of the two ligands in the column to the donor population according to the distribution of the blood groups in the latter.

The polymer particles onto which at least one oligosaccharide corresponding to a blood group A epitope is grafted, and the polymer particles onto which at least one oligosaccharide corresponding to a blood group B epitope is grafted, can also, if appropriate, be mixed with polymer particles bearing both at least one oligosaccharide corresponding to a blood group A epitope, and at least one oligosaccharide corresponding to a blood group B epitope.

Advantageously, the matrix selected does not lead to undesired activation of the coagulation factors present in the plasma to be treated.

Immunoaffinity chromatography or in batch depletion:

The matrix as defined here is used in immunoaffinity chromatography or in batch depletion binding anti-A and anti-B antibodies.

According to the matrix used, the following will be obtained:

either a thus-named "anti-A" matrix i.e. containing only polymer particles onto which only oligosaccharides corresponding to a blood group A epitope are grafted or a thus-named "anti-B" matrix i.e. containing only polymer particles onto which only oligosaccharides corresponding to a blood group B epitope are grafted or a thus-named "anti-A anti-B" matrix i.e. containing both polymer particles onto which at least one oligosaccharide corresponding to a blood group A epitope is grafted, and polymer particles onto which at least one oligosaccharide corresponding to a blood group B epitope is grafted.

In a particular embodiment, the matrices have the following formulae:

support-spacer-ligand (trisaccharide).

In a particular embodiment, the matrices have the following formulae:
"Anti-A" matrix:
    support-spacer-trisaccharide corresponding to the blood group A epitope,
"Anti-B" matrix:
    support-spacer-trisaccharide corresponding to the blood group B epitope,
Matrix "anti-A and anti-B":
    support-spacer-trisaccharide corresponding to the blood group A epitope and support-spacer-trisaccharide corresponding to the blood group B epitope
More particularly:
"Anti-A" matrix:
    (polymer particle)—NH—$C_5H_{10}$—CO—NH—$C_3H_6$-(N-acetylGal$\alpha_{1-3}$(Fuc$\alpha_{1-2}$)Gal)
"Anti-B" matrix:
    (polymer particle)—NH—$C_5H_{10}$—CO—NH—$C_3H_6$-(Gal$\alpha_{1-3}$((Fuc$\alpha_{1-2}$)Gal)
Matrix "anti-A and anti-B":
    (polymer particle)—NH—$C_5H_{10}$—CO—NH—$C_3H_6$-(N-acetylGal$\alpha_{1-3}$(Fuc$\alpha_{1-2}$)Gal) and (polymer particle)—NH—$C_5H_{10}$—CO—NH—$C_3H_6$-(Gal$\alpha_{1-3}$((Fuc$\alpha_{1-2}$)Gal)

The matrix can be introduced into a chromatography column. On an industrial scale, the column can contain from 1 to 150 litres, advantageously from 1 to 100 litres preferentially from 1 to 50 litres. In the case of implementation on a pilot scale, it is possible to use columns from 1 to 50 cm in height, the diameter is then adapted to the height of column used. The volume of matrix used in the column is adjusted depending on the desired residual level of anti-A and/or anti-B antibodies compared to the initial level of anti-A and/or anti-B antibodies in the solution.

The anti-A and/or anti-B antibodies present in the plasma bind to the matrix, and the non-adsorbed product (plasma) is recovered, poor in anti-A and/or anti-B antibodies. The plasma is poured through the matrix at a speed and under conditions which allow the binding of the antibodies with the ligands borne by the matrix.

The matrices are adapted for industrial use and can be advantageously reused repeatedly, without degradation. Their regeneration can be carried out by procedures known to a person skilled in the art, for example by treatment with sodium hydroxide (NaOH), for example at 1 M.

Advantageously, the stages of regeneration are suitable for taking account of the fouling of the column due to the passage of plasma.

Preferably, the pH of the plasma is adjusted to a pH greater than or equal to 5, advantageously greater than or equal to 6, advantageously to a pH of approximately 7.4 before the chromatography or in batch depletion.

The load of the column is suited to the sought residual level of anti-A and/or anti-B antibodies. The specificity of such a matrix does not require prior conditioning of the plasma, i.e. any fraction or plasma can be suitable. The percolation of the plasma does not involve any elution mechanism. Consequently, the plasma is percolated through the column, optionally by means of a pump. This percolation allows the retention of the anti-A and anti-B antibodies. The contact time between the ligands and the plasma is greater than or equal to 30 seconds, advantageously greater than or equal to one minute, preferentially greater than or equal to 2 minutes.

Step b) therefore allows the removal of the anti-A and B antibodies. Preferably, step b) makes it possible to achieve a residual content of anti-A and anti-B antibodies such that the result of the Coombs test is negative at a 1/64 dilution, finally making it possible to obtain a universal plasma according to the process of the invention which can be used on any recipient, independently of their blood group.

In a preferred embodiment, the universal plasma originating from step b) has an anti-A antibody content and an anti-B antibody content in accordance with a negative result in the Coombs test at a 1/64 dilution. Preferably, the anti-A antibody content is such that the result of the Coombs test is negative at a 1/32 dilution, preferably negative at a 1/16 dilution, even more preferentially negative at a 1/8 dilution or less. Preferably, the anti-B antibody content is such that the result of the Coombs test is negative at a 1/32 dilution, preferably negative at a 1/16 dilution, even more preferentially negative at a 1/8 dilution or less.

In a particular embodiment, the plasma thus depleted of anti-A and anti-B antibodies can then be subjected to a step of lyophilization (step c) or cryodesiccation or atomization. The lyophilization step is particularly difficult since the haemostatic properties of the mixture of safe plasmas should not be compromised. There is then a need to find a balance between a very low residual moisture content and the storage of the coagulation factors, which can prove particularly sensitive to the aggressive lyophilization process. Preferentially, the lyophilization step c) makes it possible to obtain a lyophilized plasma with a moisture content less than 3%, preferentially less than 2%. Typically, the lyophilization of step c) comprises several phases: freezing, primary desiccation or sublimation, and secondary desiccation or final drying.

By "lyophilization" or "cryodesiccation", is meant a low-temperature dehydration operation which consists of removing by sublimation, the majority of the water contained in a product. It allows for long-term storage due to the reduction of the activity of the water in the product.

A standard lyophilization process consists of three stages:
1) A freezing step: each formulation has a temperature that is critical for the lyophilization. They must be cooled down below this point (eutectic temperature) for optimum solidification.
    There are two types of freezing depending on the composition of the solution to be frozen:
        A slow freezing rate makes it possible to obtain a frozen solution structure having crystals of large sizes
        A rapid freezing rate makes it possible to obtain a frozen solution structure with fine crystals.
2) A step of primary desiccation in which the pressure of the drying (lyophilization) chamber is reduced allowing the sublimation of the ice. This phase is carried out at a low or high temperature according to the collapse or melting temperature of the product. Sublimation requires energy; the heat is transferred to the product through the shelves supporting the flasks and by radiation. This step allows the sublimation of the water referred to as "free". The structure of the frozen solution (therefore the freezing rate) influences the sublimation rate, in particular by modifying the vapour pressure necessary for the sublimation phenomenon.
3) A step of secondary desiccation (desorption): the temperature of the shelves is increased or maintained and the pressure of the chamber is reduced in order to allow the desorption of the water referred to as "bound" to the product. The purpose of this is to obtain a final moisture quantity suited to the storage of the product.

Lyophilization is a time- and energy-consuming process which can take several days or even several weeks to be completed (if the lyophilization cycle is not optimized). The development and optimization of lyophilization cycles are established on the basis of the critical temperatures (T'g solidification temperature, Tc collapse temperature, Tf melting temperature).

In a particular embodiment of the invention, the lyophilization comprises a preliminary step of pre-cooling, advantageously at −5° C.

In a particular embodiment of the invention, the lyophilization comprises a rapid freezing phase between −30° C. and −60° C. in which the water contained in the plasma is solidified. Typically, this freezing step has a duration of a few hours, with a step of progressively reducing the temperature in order to reach the temperature for complete solidification of the plasma to be lyophilized.

In particular, the rapid freezing phase can take place at −50° C. The freezing step is carried out with a gradient with a duration comprised between 15 minutes and 60 minutes, preferentially of approximately 30 minutes and a plateau with a duration comprised between 100 and 600 minutes, preferentially of approximately 300 minutes.

When all the plasma is frozen, the sublimation phase, also called primary desiccation takes place, which will result in the water passing from the solid form to the vapour form, without passing through a liquid form. This step takes place at low pressure and at a temperature less than the initial melting temperature, i.e. at a temperature comprised between −20° C. and 20° C. Typically, the primary desiccation step lasts a few hours. The primary desiccation phase is generally prolonged, i.e. the sublimation is continued so as to introduce a safety step into the process in order to ensure homogeneity of the product, in particular in short cycles.

The secondary desiccation step takes place at a pressure less than 300 μBar (i.e. 30 Pa) and at a temperature comprised between 10 and 15° C. Typically, the first plateau at 10° C. has a gradient with a duration comprised between 20 and 120 minutes, preferentially of approximately 60 minutes and a plateau with a duration comprised between 2000 and 4000 minutes, preferentially of approximately 3000 minutes. The second plateau at 15° C. has a gradient with a duration comprised between 5 and 60 minutes, preferentially of approximately 10 minutes and a plateau with a duration comprised between 800 and 2000 minutes, preferentially of approximately 1200 minutes.

When the primary desiccation phase is completed, the product obtained also contains the captive residual water which corresponds to the molecules of water remaining trapped in surface of a product subjected to primary desiccation. The secondary desiccation phase or final drying allows the desorption of said residual water in order to obtain minimal final moisture of the product final, at a level less than or equal to 3% by weight, in particular less than or equal to 2% by weight, with a view to storage of the product.

This final drying step is carried out at a temperature comprised between 20 and 50° C. under reduced pressure.

In particular, the final drying is carried out at a temperature comprised between 30 and 35° C. under a reduced pressure of approximately 30 μBar (i.e. 3 Pa). Typically, the first plateau at 35° C. has a gradient with a duration comprised between 2000 and 15000 minutes, preferentially 6000 minutes and a plateau with a duration comprised between 800 and 2000 minutes, preferentially 1200 minutes. The second plateau at 30° C. has a gradient with a duration comprised between 2000 and 1000 minutes, preferentially 480 minutes and a plateau with a duration comprised between 1200 and 2500 minutes, preferentially 1800 minutes.

The primary and secondary desiccation phases have durations adapted to the critical temperature of the product to be lyophilized (plasma).

Advantageously, the lyophilization protocol used makes it possible to obtain a lyophilized universal plasma with a moisture content less than 3%, preferentially less than 2%.

By "atomization" is meant a dehydration method of a liquid (milk, serum, plasma, etc.) as powder by passage through a hot air flux.

The process of the invention, independently of the presence or absence of a lyophilization or cryodesiccation or atomization step can moreover comprise a biological safety step upstream of step a) of said process. The non-universal unit plasmas constituting the mixture of plasmas of step a) of the process of the invention are made biologically safe, for example viro-inactivated by physico-chemical treatment. By "biological safety measure", is meant the elimination of the pathogenic effect of viral agents that can be present in the plasma. The "biological safety measure" can in particular cover "viral inactivation" or "viro-inactivation". This biological safety measure destroys the majority of pathogenic agents such as bacteria, enveloped or non-envelope viruses, or other unconventional pathogenic agents (prions) or prevents their replication.

In the context of this invention, the biological safety measure is preferentially carried out by physico-chemical treatment of the non-universal unit plasmas, before they are mixed. Alternatively, this biological safety measure can be carried out on the mixture of plasmas obtained in step a). The biological safety measure by physico-chemical treatment can be a treatment using a photochemical agent (UV, IR etc.) or by solvent-detergent.

In a particular embodiment of the invention, the biological safety measure is carried out by adding Amotosalem (Intercept®) and UV radiation of 5-10 min at 380-400 nm.

Preferentially, this biological safety measure is carried out by solvent/detergent treatment. Preferably the solvent/detergent used is a solvent/detergent the removal of which from the plasma of interest is facilitated due to its properties, for example a dialysable solvent/detergent or a filtrable solvent/detergent. In fact, the use of dialysable and/or filtrable solvent/detergent makes it possible to facilitate the removal of these products, unlike the non-dialysable and/or non-filtrable solvents/detergents (such as TNBP/Triton X-100®) which require dedicated removal stages, for example by vegetable oil extraction or hydrophobic chromatography adsorption. HECAMEG® (6-O-(N-Heptylcarbomoyl)-methyl-α-D-glucopyranoside) may be mentioned for example as dialysable and/or filtrable solvent/detergent.

Advantageously, the biological safety step if necessary is coupled with a step of removal of the treatment agents, for example by dialysis, by diafiltration, by filtration on an affinity filter (Plasmaflex PLAS4®, Macopharma) or by using a dedicated device (Solvent Detergent Removal® from Pall Biosepra) or adsorbent resins (SDR hyperD® resin from Pall Life Sciences)). In a particular embodiment, the step of removal of the treatment agents is carried out at a temperature comprised between 0 and 25° C., advantageously between 5 and 20° C., even more advantageously between 10 and 15° C. Temperatures less than 25° C., in particular less than 20° C., advantageously make it possible to partially or completely limit the activation of coagulation factors.

In another particular embodiment of the invention, the biological safety step is carried out by any appropriate means known to a person skilled in the art, in particular by viral inactivation or removal methods. By viral inactivation methods is meant in particular heat treatment (pasteurization and/or heating to dryness), and/or irradiation treatment (UVC, and/or Gamma). The viral removal methods include in particular nanofiltration which can also be used to remove infectious agents, in particular viruses and UCTAs (unconventional transmissible agents). Nanofiltration generally refers to the filtration of the plasma through a filter with a pore size of less than 80 nm. The available filters are for example the BioEx®, Planova® 75 nm, Planova® 35 nm, Planova® 20 nm or Planova® 15 nm (Asahi corporation), Ultipor DV 50® or DV 20® (Pall corporation), Virosart CPV® (Sartorius), Viresolve NFR® or NFP® (Millipore) filters. The nanofiltration can be advantageously carried out on a single filter or on several filters in series, of identical or decreasing porosity, for example in a 35 nm-35 nm, 35 nm-20 nm, 20 nm-20 nm or 20 nm-15 nm sequence.

The removal of the infectious agents can also be carried out by means of depth filtration on filters The available filters are for example filters composed of regenerated cellulose, to which filtration adjuvants (such as cellite, perlite or diatomaceous earth) marketed by Cuno (Zeta+ VR series® filters), Pall-Seitz® (P-series Depth Filter®) or Sartorius (Virosart CPV®, Sartoclear P depth filters®) may have been added.

By "pathogenic agent", is meant a viral, bacterial or unconventional pathogen-type contaminant (prion). The presence of such contaminants is unacceptable for the use of a plasma in therapy.

By "biologically safe plasma" or "viro-inactivated plasma" is meant a plasma which has undergone a biological safety step, for example by inactivation, i.e. the actual destruction or inhibition of the replication of pathogenic agents such as viral, bacterial contaminants or unconventional pathogenic agents. In a particular embodiment, the mixture of plasmas of step a) of the process of the invention are inactivated by solvent/detergent. Such a plasma inactivation technique is particularly advantageous since it allows the plasma to be made biologically safe by simply adding solvent/detergent under conditions allowing the storage of all of the other plasma constituents. The operating conditions allowing the removal of pathogenic agents using solvent/detergent while retaining the other plasma constituents are known to a person skilled in the art. According to the invention, this technique for the removal of pathogenic agents is preferentially applied to each unit plasma collected by aphaeresis. In another embodiment, the technique for the removal of pathogenic agents is advantageously applied to the pool of plasma.

In a particular embodiment of the invention, an additional step can be added in order to adjust the physico-chemical properties and restore physico-chemical properties similar or close to those of an untreated plasma. In particular, the ionic balance, pH and osmolarity must be maintained at physiological levels compatible with administration to patients. Apart from being in accordance with the methods used in the process according to the invention, certain parameters, such as the ionogram, can be slightly altered, in particular for example during diafiltration steps. A step making it possible to restore the physico-chemical properties of normal plasma, for example the ionogram, are therefore particularly advantageous.

The process of the invention can also comprise a step of sterilizing filtration or clarifying filtration on a 0.45 μm and/or 0.2 μm filter, for example on a polypropylene filter or equivalent media such as the ProFile (Pall) filter.

The process of the invention can moreover comprise an ultrafiltration step upstream of step a) of said process aimed at removing the bacteria and the solvent-detergent optionally used in order to inactivate the plasma. The unit plasmas constituting the mixture of plasmas of step a) of the process of the invention are ultrafiltered in order to remove the bacteria potentially present in the plasma. The ultrafiltration can advantageously comprise a step of dialysis in order to remove the solvent-detergent used for the inactivation of the plasma.

In the context of this invention, the removal of the bacteria is carried out by ultrafiltration of the unit plasmas, before they are mixed. Alternatively, this removal of bacteria can be carried out on the mixture of plasmas obtained in step a).

According to the invention, this technique for the removal of the bacteria by ultrafiltration is preferentially applied to each unit plasma collected by aphaeresis. In another embodiment of the invention, the removal of the bacteria by ultrafiltration is applied to the pool of plasma.

In a particular embodiment of the invention, the ultrafiltration step is carried out so as to completely or partially limit the activation of coagulation factors.

The present invention also relates to an universal plasma obtained according to the process described above.

The invention also relates to a lyophilized universal plasma that is compatible with all the blood groups. Preferentially, the lyophilized universal plasma of the invention is characterized in that it comprises a mixture of plasmas collected from donor individuals belonging to blood groups A, B, AB and/or O. This lyophilized plasma has a moisture content less than 3%, preferentially less than 2%. It is moreover characterized in that it can be stored at ambient temperature or in a refrigerated enclosure at a temperature comprised between +2° C. and +30° C. and for a duration greater than a year, preferentially of at least 2 years.

Preferentially, the lyophilized universal plasma of the invention is characterized in that it comprises an anti-A and/or anti-B antibody content such that the result of the Coombs test is negative at a 1/64 dilution. Preferably, the anti-A antibody content of the lyophilized universal plasma of the invention is such that the result of the Coombs test is negative at a 1/32 dilution, preferably negative at a 1/16 dilution, even more preferentially negative at a 1/8 dilution or less. Preferably, the anti-B antibodies content of the lyophilized universal plasma of the invention is such that the result of the Coombs test is negative at a 1/32 dilution, preferably negative at a 1/16 dilution, even more preferentially negative at a 1/8 dilution or less. Preferentially, this lyophilized blood plasma is sterile.

Advantageously, the lyophilized blood plasma is poor in endotoxins.

The invention also relates to a process for the preparation of reconstituted plasma comprising the step of reconstitution of the lyophilized plasma, made biologically safe, and compatible with all the blood groups, in a reconstitution solvent. The reconstitution of the plasma thus makes it possible to obtain an injectable preparation, can be administered to any recipient under emergency conditions.

Typically, the reconstitution of the plasma is carried out in a volume of reconstitution solvent comprised between 10 and 500 mL, preferentially from 100 to 300 mL. Typically, this reconstitution is carried out with a volume making it possible to obtain an iso-osmotic plasma.

Preferentially, this reconstitution solvent is water and more preferentially water for injection. Preferentially, the reconstitution of the lyophilized plasma in order to obtain an injectable preparation is carried out within a duration of less than 6 minutes, preferentially less than 3 minutes.

Also, the use of the plasma according to the invention is very advantageous and avoids the time needed for thawing when fresh frozen plasma is used.

The invention also relates to a reconstituted, biologically safe plasma that is compatible with all the blood groups and can be injected directly. Such a reconstituted plasma can be administered to any individual, independently of their blood group. It is therefore highly suitable for use under emergency conditions, in particular for the treatment of haemorrhagic emergencies with coagulopathy, in particular in isolated situations with logistic conditions making it impossible to control a negative cold chain.

The reconstituted plasma according to the invention moreover has the advantage of destroying most pathogenic agents which considerably reduces the potential diffusion of pathogenic agents to the recipient individuals. This reconstituted plasma meets all the regulatory requirements governing the plasmas used in therapy.

The reconstituted plasma of the invention is characterized in that the concentration of factor VIII is greater than 0.5 IU/mL, preferentially greater than 0.7 IU/mL.

The reconstituted plasma of the invention is characterized in that the concentration of factor V is greater than 0.15 IU/mL, and preferentially comprised between 0.7 and 1.2 IU/mL. The international units (IU) for the coagulation factors express the plasma activity of the proteins to which this expression is applied. An international unit (IU) of these plasma proteins correspond to the quantity of this factor contained in one mL of normal human plasma.

The reconstituted plasma of the invention is characterized in that the concentration of fibrinogen is greater than 1 g/L and more preferentially comprised between 2 and 4 g/L.

The reconstituted plasma of the invention is characterized in that it is sterile and apyrogenic.

Of course, the present invention is not limited to the embodiments described and represented, but it is capable of numerous variants accessible to a person skilled in the art.

FIGURES

FIGS. 1A and 1B: these figures show respective results of factor V dosage (FIG. 1A) and of factor VIII (FIG. 1B) present in univsersal plasma obtained from human donor individuals belonging to blood groups A, B, AB and O after immunoaffinity chromatography, in starting plasma and in non retained fractions (NRF) 1-4.

FIG. 2A and 2B: these figures show respective results of factor V (FIG. 2A) and of factor VIII (FIG. 2B) present in univsersal plasma obtained from human donor individuals belonging to blood group O after immunoaffinity chromatography, in starting plasma and in non retained fractions (NRF) 1-14.

Figure 5A:
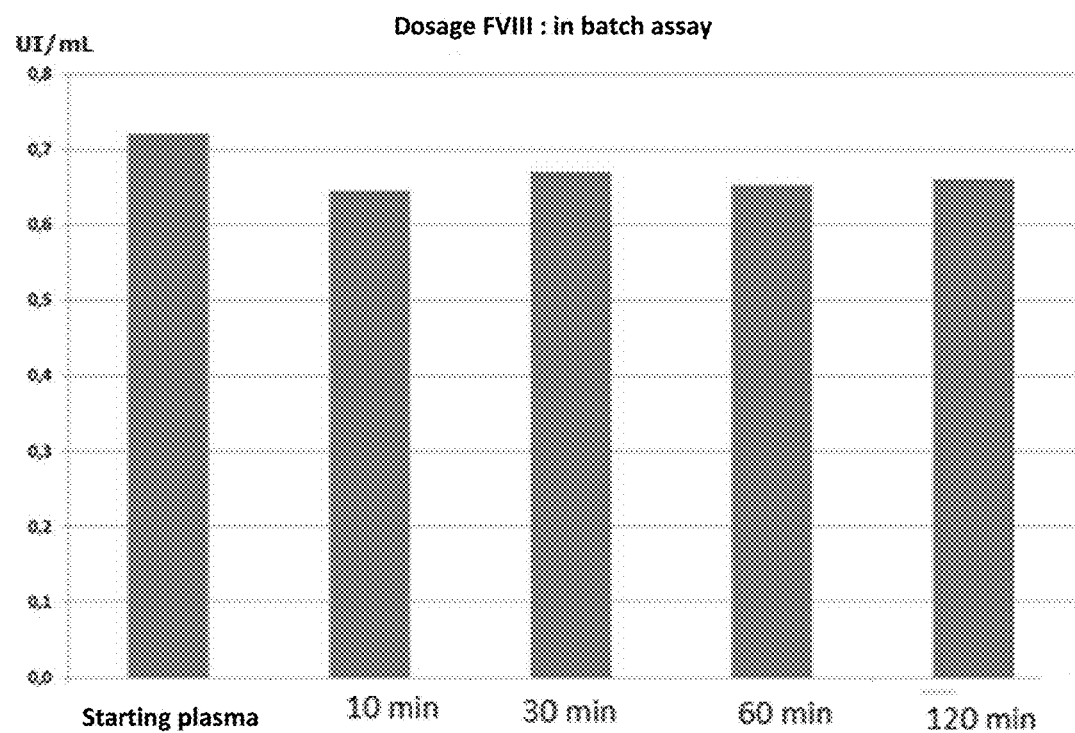
Figure 5B:
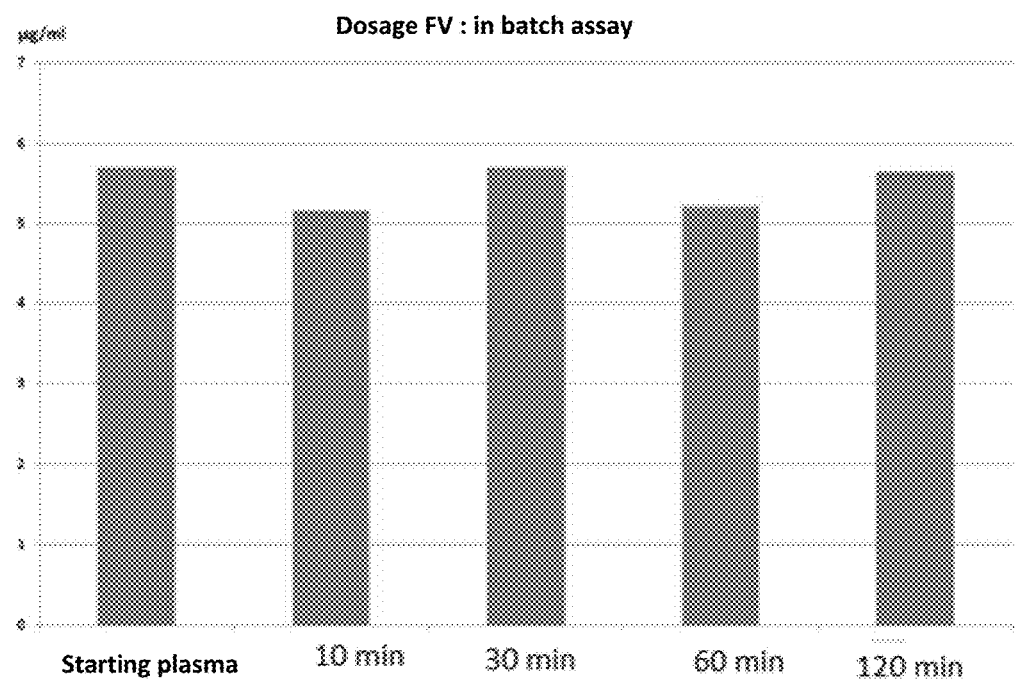

FIGS. 5A and 5B: these figures show respective results of factor VIII dosage (FIG. 5A) and of factor V (FIG. 5B) present in universal plasma obtained from human donor individuals belonging to blood group O after in batch depletion, in starting plasma and collections after 10 min, 30 min, 1 h and 2 h incubation, respectively.

Figure 6:
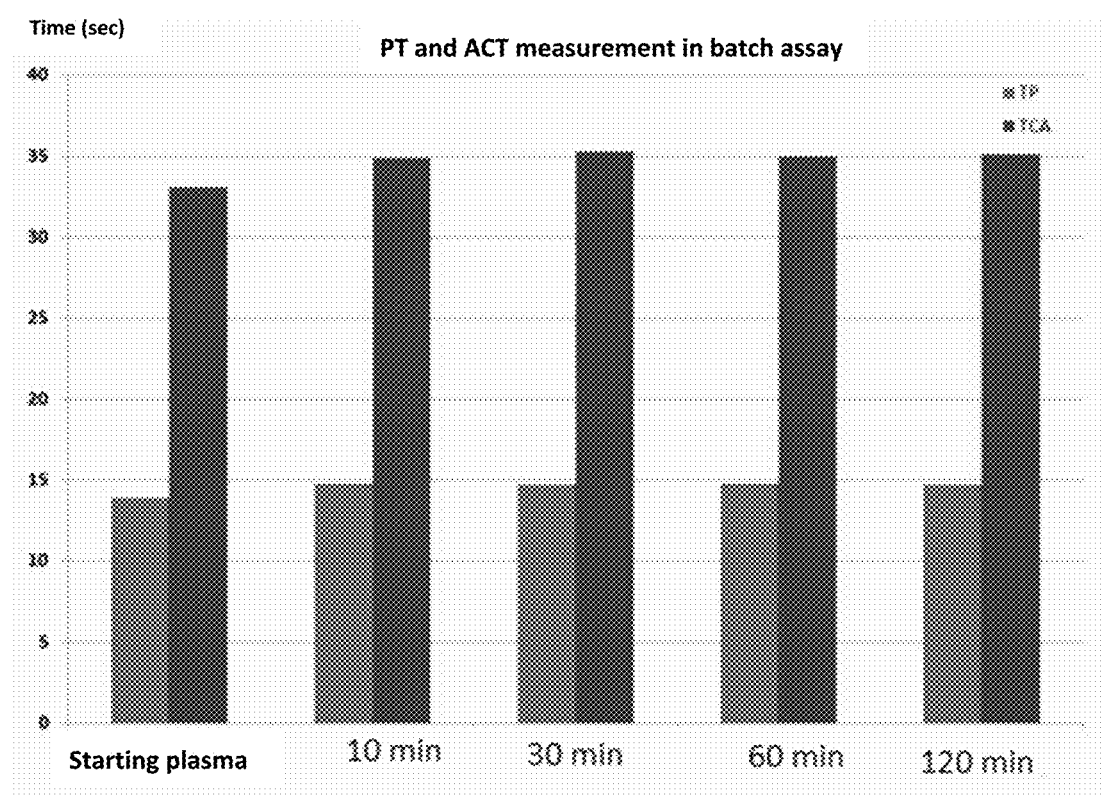

FIG. 6 shows the results of quick time measurement and of activated cephalin time measurement of universal plasma obtained from human donor individuals belonging to blood group O after in batch depletion, in starting plasma and collections after 10 min, 30 min, 1 h and 2h incubation.

EXAMPLES

Example 1

Preparation of Universal Plasma from Human Donor Individuals Belonging to A, B, AB and O Blood Groups A/ Collection of Non-universal Unit Plasma Approximately 200 mL of plasma from human donor individuals belonging to blood groups A, B, AB and O is collected by aphaeresis. During collection of the plasma, leucocyte depletion of said non-universal unit plasmas is carried out by centrifugating twice at 1500 g for 10 min.

The non-universal unit plasmas are then subjected to a step of making them biologically safe by treating said plasma with Amotosalem (Intercept®): 15 mL of Amotosalem at 150 µM are added into each non-universal unitary plasma, which are further treated during 5-10 min by UVA irradiation at wavelength from 380 to 400 nm. The residual Amotosalem and photoproducts are then eliminated by filtration through adsorbent filter to reach a residual Amotosalem content lower than 2 µM. Then said attenuated non-universal unit plasmas are deep-frozen over the 8 hours following collection of the plasmas. This step then allows storage of said plasmas at a temperature of −25° C. 15 minutes before the plasmas are mixed, the plasmas are placed in a water bath at 37° C. to thaw.

B/ Mixture of the Non-universal Unit Plasmas

The mixture of plasmas is prepared by mixing the non-universal unit plasmas obtained from human donor individuals belonging to blood groups A, B, AB and O. For example, for the mixture, the following is used:

6 bags of plasma (1327 mL of plasma) obtained from 3 different donor individuals belonging to blood group A, 6 bags of plasma (1327 mL of plasma) obtained from 3 different donor individuals belonging to blood group B, and 6 bags of plasma (1327 mL of plasma) obtained from 3 different donor individuals belonging to blood group AB, and 6 bags of plasma (1327 mL of plasma) obtained from 3 different donor individuals belonging to blood group O.

In this way a mixture comprising 5308 mL of non-universal plasmas is obtained.

C/ Step of Removal of the Anti-A and Anti-B Antibodies Present in the Plasma The mixture of non-universal plasmas obtained in the previous step is subjected, on an industrial scale, to an anti-A/anti-B affinity chromatography step carried out on a column comprising a 50/50 (v/v) mixture of cross-linked cellulose beads onto which trisaccharides corresponding to a blood group A epitope (N-acetylgalactosamine (GalNAc)-Galactose(Gal)-Fucose) are grafted, designated Iso A HyperCel® gel, and cross-linked cellulose beads onto which trisaccharides corresponding to a blood group B epitope (Galactose-Galactose-Fucose) are grafted, designated Iso B HyperCel® gel.

The trisaccharides are grafted onto the beads by means of a spacer of formula:

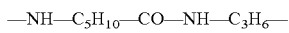

The matrix used has the following formula:

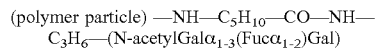

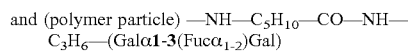

The density of grafted trisaccharides is 0.3 mg per ml of matrix gel.

The mixture of plasma was passed through a 5.5 ml column (comprising 2.75 ml of Iso A HyperCel® gel+2.75 ml of Iso B HyperCel® gel)

Format of the column: D=1 cm×7 cm (column volume (CV)=5.5 ml).

The column is stabilised in saline phosphate buffer PBS.

Contact time: 2.5 min Load: 165 mL of plasma mixture at a rate of flow of 2 mL/min. The effluent (4 non-retained fractions) is recovered in fractions of 45 mL. The collection is stopped at the end of injection to avoid plasma dilution.

Assay Tests:

The residual anti-A and anti-B activity, corresponding to the percentage of anti-A and anti-B isoagglutinins present in the final plasma preparation compared to their concentration before the affinity chromatography step, was measured by flow cytometry (a sensitive and accurate technique), according to the technique described below.

The wells of a V-shaped bottom plate are saturated by 125 µL of PBS with 2% of fetal bovine serum (FBS) during 1 h at 37° C. 100 µL of AB group red blood cells suspension are then added (PBS+2% FBS) at a rate of 0.05% per well. The plates are centrifugated during 1 min. at 100 g and the supernatant is eliminated. 100 µL of native plasma or non-retained fractions (NRF) ±diluted in PBS+2% FBS are added before incubation of 60 min. at 37° C. 6 washings are carried out by adding 150 µL in PBS +2% FBS. 100 µL of Anti IgG-PE secondary antibody is then added in PBS +2% FBS and is incubated 20 min. at 4° C. After 2 washings in PBS+2% FBS, the sample is recorded by cytometer.

The mean fluorescence intensity (MFI) of the positive control was given as a function of the plasma concentration (standard curve) for concentrations ranging from 0.23 g/L to 30 g/L. The results are expressed as the ratio between the slope of the sample and the slope of the positive standard. The equation of the standard curve is y=ax+b; where "a" is the value of the slope of the standard curve and "b", the zero point corresponding to the background noise of the test. As the equation for the sample is y'=a'x+b, and by using the known values of MFI for the sample (y') and the plasma concentration (x'), the ratio of the slopes was calculated as being [(MFI-b)/[IgG concentration]]/a.

Results:

The residual anti-A and anti-B activity obtained are presented in the table 1 below:

TABLE 1

| Fraction | % of agglutination (IgG) |
|---|---|
| Starting Plasma | 100% |
| NRF1 | 6% |
| NRF2 | 9% |
| NRF3 | 16% |
| NRF4 | 21% |

The results in this table show a significant reduction in the residual anti-A and anti-B activity (of type IgG), which is comprised between 6 and 21% after immunoaffinity.

The residual anti-A and anti-B activity is also measured by Coombs test according following method: 100 µL of 1% AB red blood suspension in physiological water are deposited on each wells of microplate then centrifugated 1 min. at 100 g. The supernatant is eliminated, then 100 µL of plasma or non retained fraction (NRF) is added ±diluted in physiological water. After 30 min incubation at 37° C. and 1 min centrifugation at 100 g, the agglutinates are recorded by gental agitation.

The results are shown in the table 2 below.

| | Agglutinats | | | | | |
|---|---|---|---|---|---|---|
| Dilutions | Starting Plasma | NRF1 | NRF2 | NRF3 | NRF4 | Serum AB |
| Dilution at 1/1 | + | + | + | + | + | − |
| Dilution at 1/2 | + | + | + | + | + | − |
| Dilution at 1/4 | + | + | + | + | + | − |
| Dilution at 1/8 | + | − | + | + | + | − |
| Dilution at 1/16 | + | − | − | + | + | − |
| Dilution at 1/32 | + | − | − | − | − | − |
| Dilution at 1/64 | − | − | − | − | − | − |
| Dilution at 1/128 | − | − | − | − | − | − |
| Dilution at 1/256 | − | − | − | − | − | − |
| Dilution at 1/512 | − | − | − | − | − | − |

These results show that the rate espressed in direct Coombs test in fractions 1 to 4 is comprised between ¼ and 1/16. The product thus obtained is then (at a dilution of 1/64) in accordance with a negative result in the direct Coombs test. In this way a universal plasma poor in anti-A and anti-B antibodies is obtained.

Content of the Coagulation Factors Present in the Universal Plasma

The activity of the coagulation factors contained in the universal plasma resulting from the immunoaffinity chromatography step was tested. The operational modes and results are presented below.

Factor V Dosage

The factor V(FV) was dosed by the Zymutest Factor V test from Hyphen Biomed, France (ref : RK009A) as recommended by the manufacturer. The test is a sandwich ELISA which uses an anti-FV antibody binded to the microwells. The citrated plasma is diluted in a provided buffer (1/100 and 2/200) and incubated during 2 h at 37° C. The plate is washed 5 times and incubated with a secondary anti-FV antibody coupled to horse radish peroxidase for 2 h at 37° C. The plate is washed 5 times and binded antibody is revealed during 5 min with a 3,3', 5,5'-tetramethylbenzidine (TMB) solution. The reaction is stopped by adding $H_2SO_4$ 0.45 M. The optic density is recorded at 450 nm during 10 min of stabilisation. A standard curve is established and two control plasmas with intermediate FV concentrations are carried out for each test.

Factor VIII Dosage

The factor VIII (FVIII) was dosed by the Asserachrom® VIII:Ag test obtained from Stago, France (ref: 00280) as recommended by the manufacturer. The test is a sandwich ELISA which uses an anti-FVIII antibody binded to the microwells. The citrated plasma is diluted in a provided buffer (1/10 and 2/20) and incubated during 2 h at room temperature. The plate is washed 5 times and incubated with a secondary anti-FVIII antibody coupled to horse radish peroxidase for 2 h at room temperature. The plate is washed 5 times and binded antibody is revealed during 5 min with a TMB solution. The reaction is stopped by adding $H_2SO_4$ 0.45 M. The optic density is recorded during 10 min of stabilisation. A standard curve is established and two control plasmas with intermediate FVIII concentrations are carried out for each test.

Figure 1A:
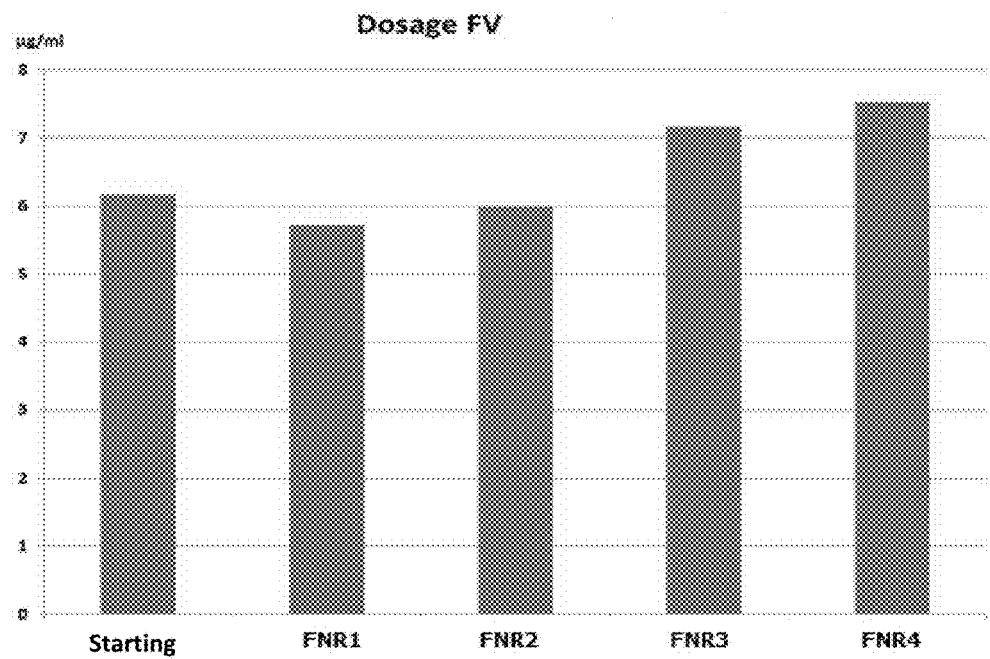
Figure 1B:
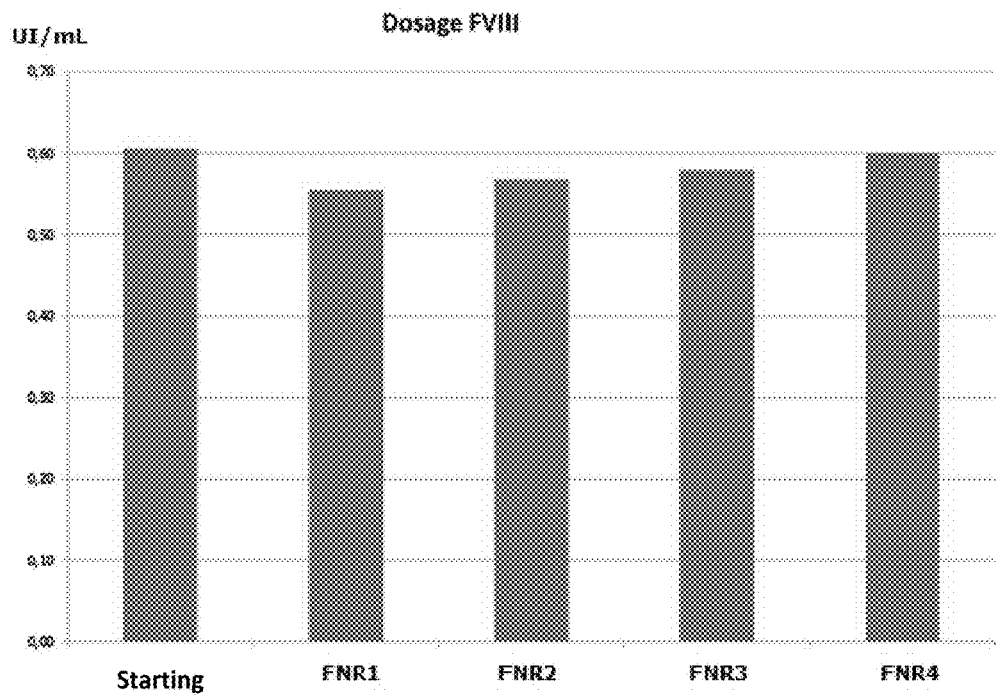

Results:

The respective dosage results of factor V and factor VIII are shown in FIGS. 1A and 1B.

The passage through the immunoaffinty chromatography column does not affect factor V and factor VIII contents within the plasma. The universal plasma obtained shows a content of factor V greater than 5 µg/mL and a content of factor VIII greater than 0.5 IU/mL.

Example 2

Preparation of Universal Plasma from Human Donor Individuals Belonging to O Blood Group with the Help of Immunoaffinity Chromatographie A/ Collection of Non-universal Unit Plasma Approximately 500 mL of plasma from human donor individuals belonging to blood group O is collected by aphaeresis.

During collection of the plasma, leucocyte depletion of said non-universal unit plasmas is carried out by 2 times centrifugation at 1500 g during 10 min.

The non-universal unit plasmas are then subjected to a step of making them biologically safe by treatment of Amotosalem (Intercept®): 15 mL of Amotosalem at 150 µM are added into each non-universal unitary plasma, which are further treated during 5-10 min by UVA irradiation at a wavelength of 380-400 nm. The residual Amotosalem and phtoproducts are then eliminated by filtration acrosse adsorbent filter for arriving to a residual Amotosalem level of lower than 2 µM.

Then said attenuated non-universal unit plasmas are deep-frozen over the 8 hours following collection of the plasmas. This step then allows storage of said plasmas at a temperature of −25° C.

15 minutes before the plasmas are mixed, the plasmas are placed in a water bath at 37° C. to thaw.

B/ Mixture of the Non-universal Unit Plasmas

The mixture of plasmas is prepared by mixing 75 mL of three non-universal unit plasmas obtained from human donor individuals belonging to blood group O.

A mixture comprising 225 mL of non-universal plasma.

C/ Step of Removal of the Anti-A and Anti-B Antibodies Present in the Plasma

The mixture of non-universal plasmas obtained in the previous step is subjected, on an industrial scale, to an anti-A/anti-B affinity chromatography step carried out on a column comprising a 50/50 (v/v) mixture of cross-linked cellulose beads onto which trisaccharides corresponding to a blood group A epitope (N-acetylgalactosamine (GalNAc)-Galactose(Gal)-Fucose) are grafted, designated Iso A HyperCel® gel, and cross-linked cellulose beads onto which trisaccharides corresponding to a blood group B epitope (Galactose-Galactose-Fucose) are grafted, designated Iso B HyperCel® gel.

The trisaccharides are grafted onto the beads by means of a spacer of formula:

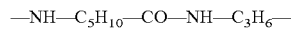

The matrix used has the following formula:

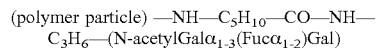

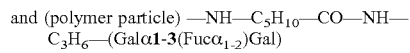

The density of grafted trisaccharides is 0.3mg per ml of matrix gel.

The mixture of plasma was passed through a 5.5 ml column (comprising 2.75 ml of Iso A HyperCel® gel +2.75 ml of Iso B HyperCel® gel)

Format of the column: D=1 cm×7 cm (column volume (CV)=5.5 ml).

The column is stabilised in buffer PBS.

Contact time: 5 min

Load: 20 mL of plasma mixture at a rate of flow of 1 mL/min.

The effluent (14 fractions no retained fractions) is recovered in fractions of 50 mL. The collection is stopped at the end of injection to avoid plasma dilution.

Assay Tests:

The residual anti-A and anti-B activity, corresponding to the percentage of anti-A and anti-B isoagglutinins present in the final plasma preparation compared to their concentration before the affinity chromatography step, was measured by flow cytometry (a sensitive and accurate technique), according to the technique described below.

The wells of a V-shaped bottom plate are saturated by 125 µL of PBS with 2% of fetal bovine serum (FBS) during 1 h at 37 ° C. 100 µL of AB group red blood cells suspension are then added (PBS+2% FBS) at a rate of 0.05% per well. The plates are centrifugated during 1 min. at 800 rev/min and the supernatant is eliminated. 100 µL of native plasma or non retained fractions (NRF) +/− diluted en PBS +2% FBS are added before incubation of 60 min. at 37° C. 6 washings are carried out by adding 150 µL in PBS +2% FBS. 100 µL Anti IgG-PE secondary antibody in PBS +2% FBS is then added before incubation 20 min. at 4° C.

After 2 washings in PBS +2% FBS, the sample is recorded by cytometer.

The mean fluorescence intensity (MFI) of the positive control was given as a function of the plasma concentration (standard curve) for concentrations ranging from 0.23 g/L to 30 g/L. The results are expressed as the ratio between the slope of the sample and the slope of the positive standard. The equation of the standard curve is y=ax+b; where "a" is the value of the slope of the standard curve and "b", the zero point corresponding to the background noise of the test. As the equation for the sample is y'=a'x+b, and by using the known values of MFI for the sample (y') and the plasma concentration (x'), the ratio of the slopes was calculated as being [(MFI-b)/[IgG concentration]]/a.

Results:

residual anti-A and anti-B activity obtained are presented in the table 3:

TABLE 3

| Fraction | % of agglutination (IgM) | % of agglutination (IgG) |
|---|---|---|
| Starting Plasma | 100 | 100 |
| FNR1 | 9 | 7 |
| FNR2 | 11 | 9 |
| FNR3 | 12 | 9 |

The results in this table show a significant reduction in the residual anti-A and anti-B activities, which are comprised between 9 and 12% (IgM) and between 7 and 9% (IgG) after immunoaffinity. The immunoaffinity chromatography enables to remove at least 80% of anti-A and anti-B of types IgG and IgM of a plasma, even if their initial rates in starting plasma are very low.

The residual anti-A and anti-B activity is also measured by Coombs test according to following method:

100 μL of 1% AB red blood suspension in physiological water are deposited on each well of microplate then centrifugated 1 min. at 100 g. The supernatant is removed, then we add 100 μL of plasma or non retained fraction (NRF) ±diluted in physiological water. After 30 min incubation at 37° C. and 1 min centrifugation at 100 g, the agglutinins are recorded by gental agitation.

The results are displayed below in table 4:

TABLE 4

| | Agglutinins | | | | | | | | |
|---|---|---|---|---|---|---|---|---|---|
| Dilutions | Plasma N°2 | Tube 3 | Tube 4 | Tube 5 | Tube 7 | Tube 10 | Tube 13 | Sérum AB | Plasma AB |
| 1/1 | + | − | +/− | +/− | +/− | +/− | +/− | − | − |
| 1/2 | + | − | − | − | − | − | − | − | − |
| 1/4 | +/− | − | − | − | − | − | − | − | − |
| 1/8 | − | − | − | − | − | − | − | − | − |
| 1/16 | − | − | − | − | − | − | − | − | − |
| 1/32 | − | − | − | − | − | − | − | − | − |
| 1/64 | − | − | − | − | − | − | − | − | − |
| 1/128 | − | − | − | − | − | − | − | − | − |

The results show that even in very low initial measured content by Coombs test (below than 1/4 in initial plasma), the immunoaffinity chromatography enables to reduce anti-A and anti-B contents in the plasma to lower or equal to a content of 1/1 measured by test Coombs.

The product thus obtained is then (at a dilution of 1/64) in accordance with a negative result in the direct Coombs test.

In this way a universal plasma poor in anti-A and anti-B antibodies is obtained.

Content of the Coagulation Factors Present in the Universal Plasma

The activity of the coagulation factors contained in the universal plasma resulting from the immunoaffinity chromatography step was tested. The results are presented below.

Factor V Dosage

The factor V(FV) has been dosed according to the dosage protocol described in Example 1.

Factor VIII Dosage

The factor VIII(FVIII) has been dosed according to the dosage protocol described in Example 1.

Figure 2A:
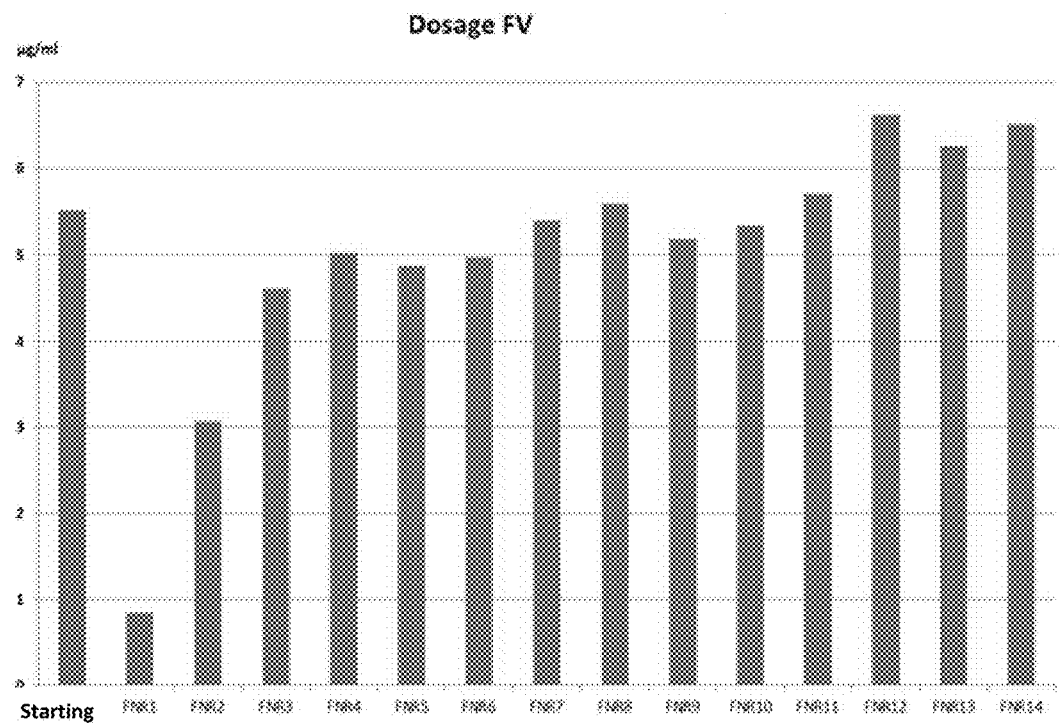
Figure 2B:
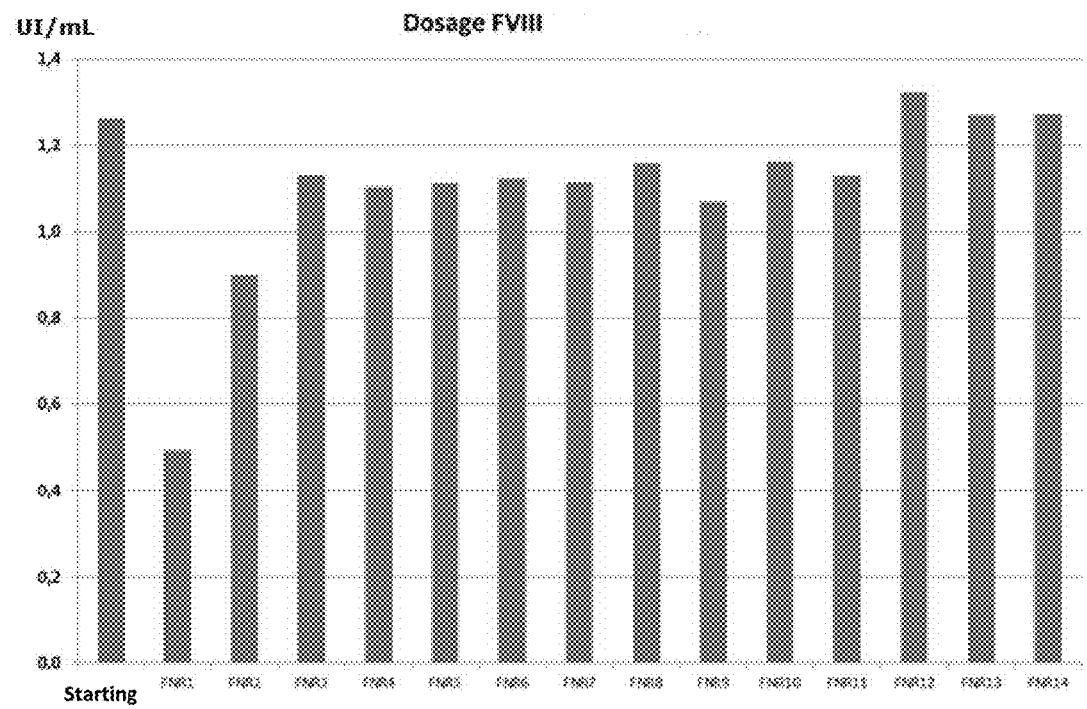

Results:

The respective dosage results of factor V and of factor VIII are displayed in FIGS. 2A and 2B.

The passage through immunoaffinity chromatography column does not affect the rates of factor V and of factor VIII of plasma. Only a slight decrease of rates of factor V and of factor VIII is noted in the first fractions (NRF1-2) which are diluted by the buffer contained in dead volume of the column. The other fractions are not affected by this phenomenon of dilution.

The obtained universal plasma has a content of factor V greater than 4 μg/mL and a content of factor VIII greater than 0.5 IU/mL.

This result is also confirmed by Quick time measurement and activated cephalin time (ACT) measurement according to the protocols described below:

Measurement of Quick Time (PT)

Quick time is measured with the help of Neoplastine CI kit (ref: 00605; Stago, France) on a device of type STAR (Stago) following the dedicated program. In short, pure citrated plasma is used. The Neoplastine® (thromboplastine prepared from fresh brain tissue of rabbit) is mixed with a solution of 25 mM calcium and is served as initiator of coagulation. After an incubation at 37° C. the plasma and coagulation indicator are mixed by a biorobot and the time of coagulation is measured and compared to a series of dedicated controls (STA coag control; ref: 00678; Stago).

Measurement of activated cephalin time (ACT)

The ACT is measured with the help of STA CK prest kit (ref: 00597; Stago, France) on a device of type STAR (Stago) following the dedicated program. In short, pure citrated plasma is used. The prepared cephalin (platelet substitute prepared from rabbit brain tissue) is mixed with a solution of kaolin (5 mg/mL) and is served as initiator of coagulation. After an incubation at 37° C. the plasma and coagulation indicator are mixed by a biorobot and the time of coagulation is measured and compared to a series of dedicated controls (STA coag control; ref: 00679; Stago).

Figure 3:
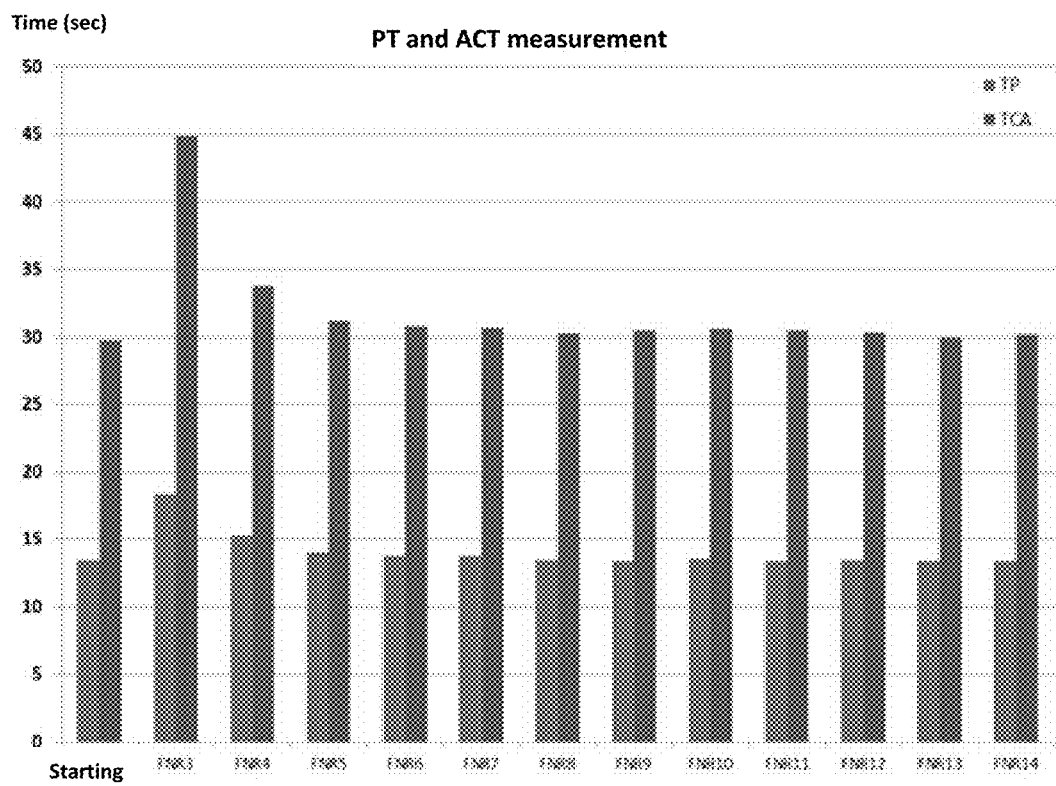
FIG. 3 shows the results of quick time (PT) measurement and of activated cephalin time (ACT) measurement of universal plasma obtained from human donor individuals belonging to blood group O after immunoaffinity chromatography, in starting plasma and in non retained fractions (NRF) 1-14.

Results:

The results are displayed in FIG. 3.

The non diluted fractions coagulate as starting plasma. The passage through immunoaffinity chromatography column does not affect plasma coagulation capacity (PT and ACT) except for fractions (NRF 3-4) which are deluted by the buffer contained in dead volume of the column.

Example 3

Preparation of Universal Plasma from Human Donor Individuals Belonging to O Blood Group with Help of in Batch Depletion The collection of non-universal unit plasma is carried out according to the method described in Example 2.

The mixture of non-universal unit plasma is obtained according to the method described in Example 2.

The removal of anti-A and anti-B antibodies present in the mixture of non-universal unit plasma is carried out by in batch depletion according to the method below:
- take 4mL of Iso A HyperCel® gel and 4 mL of Iso B HyperCel® gel and mix the 2 gels by gentil agitation.
- take 5,5 mL of gel mixture obtained before for in batch capture
- wash the gel mixture with 5 CV (column volume) of 2M NaCl solution
- wash the gel mixture with 4 CV of 0.1 M phosphate solution at pH8
- wash the gel mixture with 10 CV of ultrapure water
- stabilize the gel mixture with 5 CV of PBS filtered by a filter of 0.22 μm,
- add 20 mL of plasma pool in the gel mixture and place it under agitation at room temperature
- respectively take 1 mL of mixture of gel-plasma after 10 min, 30 min, 1 h and 2 h of incubation, that is to say 4 fractions
- recover the plasma from these fractions by centrifugation at 2300 g during 5 min.

Assay Tests:

The quantity of total proteins present in recovered plasma after in batch anti-A/anti-B depletion is measured.

Figure 4:
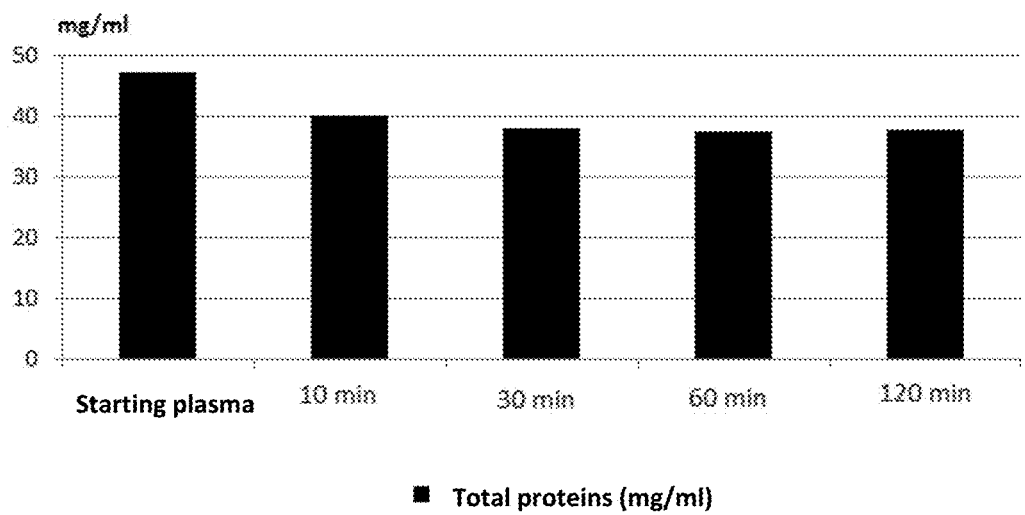
FIG. 4 shows the result of dosage of total protein present in universal plasma obtained from human donor individuals belonging to blood group O after in batch depletion, in starting plasma and collections after 10 min, 30 min, 1 h and 2 h incubation, respectively.

The result displayed in FIG. 4 shows that the quantity of total proteins only slightly decreases after in batch anti-A/anti-B depletion. This decrease is not influenced by incubation time with A HyperCel® gel and B HyperCel® gel.

The quantity of anti-A and anti-B antibodies present in the collections respectively obtained after 10 min, 30 min, 60 min and 120 min of in batch incubation has been dosed. The dosage result is given in Table 5 below.

TABLE 5

| Collections | 10 min of incubation | 30 min of incubation | 60 min of incubation | 120 min of incubation |
|---|---|---|---|---|
| % IgG 100% = starting plasma | <1.55 | <1.55 | <1.55 | <1.55 |
| % IgM 100% = starting plasma | 10 | 7 | 6 | 5 |

These results show that IgG and IgM types of anti-A and anti-B antibodies are mostly eliminated after 10 min of in batch incubation.

Content of the Coagulation Factors Present in the Universal Plasma

The activity of the coagulation factors contained in the universal plasma resulting from the immunoaffinity chromatography step was tested. The results are presented below.

The factor V (FV) and the factor VIII (FVIII) have been dosed according to the dosage protocols described in Example 1.

The results are displayed in FIGS. 5A and 5B. The anti-A/anti-B in batch depletion does not affect the contents of factor V and of factor VIII of plasma resulting from in batch depletion step.

The obtained universal plasma has a content of factor V greater than 5 μg/mL and a content of factor VIII higher than 0.6 IU/mL.

This result is also confirmed by Quick time measurement and activated cephalin time (ACT) measurement according to the protocols described in example 2.

These results are displayed in FIG. 6. These result show that anti-A/anti-B in batch depletion does not affect plasma coagulation capacity (PT and ACT).

Example 4

Lyophilization of the Universal Plasma

The universal plasma originating from the immunoaffinity chromatography step is distributed into 500 mL "type I" flasks, so that each of the flasks contains 215 mL of universal plasma.

The lyophilization of the universal plasmas contained in each of the flasks obtained previously is carried out in an SMH 615 type lyophilizer, marketed by USIFROID. Each flask is placed on a shelf. The lyophilization is carried out under specific conditions detailed below.

A/Pre-cooling

This step allows the shelves of the lyophilizer to be cooled down to a temperature of −5° C. This step makes it possible to avoid degradation of the coagulation factors which are heat-sensitive during the distribution time. The batches are loaded progressively into the lyophilizer.

B/Freezing

The universal plasma is frozen at a temperature of −50° C. The product is maintained at this temperature for 240 minutes. The duration of the gradient is 30 minutes and the plateau is 300 minutes.

C/Placing under vacuum

In order to allow sublimation, the lyophilizer is placed under vacuum. The vacuum is maintained for 2 minutes at a pressure of 600 mBar (i.e. $0.6 \times 10^5$ Pa).

D/Sublimation

This step is carried out at a temperature comprised between 10 and 15° C. and at a pressure of less than 300 μBar (30 Pa).

The first plateau at a temperature of 10° C. has a gradient of 60 minutes and a plateau of 3000 minutes.

The second plateau with a temperature of 15° C. has a gradient of 10 minutes and a plateau of 1200 minutes.

E/Secondary desiccation

This step is carried out at a temperature comprised between 30 and 35° C. under a pressure of 30 μBar (i.e. 3 Pa).

The first plateau at 35° C. has a gradient of 600 minutes and a plateau of 1200 minutes.

The second plateau at 30° C. has a gradient of 480 minutes and a plateau of 1800 minutes.

F/Lyophilisate Quality Controls

This protocol allows a lyophilized plasma to be obtained having a relative moisture level of less than 2%.

Example 5

Reconstitution of the Universal Plasma

A 500 mL flask of universal plasma is taken and 200 mL of water for injection is added. A reconstituted universal plasma is thus obtained.

After reconstitution, the product obtained must meet the following requirements:
reconstitution time of less than 6 minutes; factor VIII concentration greater than or equal to 0.5 IU /L;
anti-A and anti-B agglutinin titre of less than 64;

The composition and the characteristics of the plasma thus reconstituted are detailed in the table 6 below:

TABLE 6

Compositions and characteristics of the reconstituted plasma

| Parameters | Units | Reconstituted universal plasma |
|---|---|---|
| Fibrinogen | g/L | 2.4 |
| Factor V | IU/mL | 0.7 |
| Factor VIII | IU/mL | 0.7 |
| Factor XI | IU/mL | 0.7 |
| Protein C | IU/mL | 0.9 |
| Protein S | IU/mL | 0.9 |
| Antithrombin III | IU/mL | 1.0 |
| A2 antiplasmin | IU/mL | 0.9 |
| Anti-A titre | | <1/64 |
| Anti-B titre | | <1/64 |
| Reconstitution time | min | <6 min |

The criteria measured are in accordance with the regulatory requirements. The plasma obtained according to the process of the invention is therefore suitable for a therapeutic use.

The invention claimed is:

1. A process for the preparation of a lyophilized or atomized universal plasma, comprising:
   a) mixing non-universal unit plasmas obtained from a sample from donor individuals,
   b) simultaneously removing anti-A and anti-B antibodies present in the plasma by immunoaffinity chromatography or by in batch depletion to obtain a universal plasma, and
   c) lyophilizing or atomizing the universal plasma obtained from step b);
   wherein said step a) is carried out with no prior selection of said donor individuals.

2. A process for the preparation of a lyophilized or atomized universal plasma according to claim 1, wherein step b) is carried out by immunoaffinity chromatography or by in batch depletion on a support grafted with oligosaccharide groups antigenically similar to blood groups A and B.

3. A process for the preparation of a lyophilized or atomized universal plasma according to claim 2, wherein the oligosaccharide groups are trisaccharides corresponding to the epitopes of blood groups A and B.

4. A process for the preparation of a lyophilized or atomized universal plasma according to claim 3, wherein trisaccharides corresponding to the blood group A epitope have the structure N-acetylgalactosamine (GalNAc)—Galactose (Gal)—Fucose (Fuc), and trisaccharides corresponding to the blood group B epitope have the structure Galactose-Galactose-Fucose.

5. A process for the preparation of a lyophilized or atomized universal plasma according to claim 1, wherein the donor individuals belong to a blood group selected from blood group A, blood group B, blood group AB, and/or blood group O.

6. A process for the preparation of a lyophilized or atomized universal plasma according to claim 1, wherein the donor individuals belong to blood group A, blood group B, blood group AB, and blood group O.

7. A process for the preparation of a lyophilized or atomized universal plasma according to claim 1, wherein the universal plasma originating from step b) has an anti-A antibody content and an anti-B antibody content in the universal plasma such that the result of the Coombs test is negative at a 1/64 dilution measured according to the method described in chapter 2.6.20 of the European Pharmacopoeia 07/2011.

8. A process for the preparation of a lyophilized or atomized universal plasma according to claim 1, further comprising a biological safety step.

9. A process for the preparation of a lyophilized or atomized universal plasma according to claim 8, wherein the biological safety step is carried out by viral inactivation by a solvent and detergent treatment.

10. A process for the preparation of a lyophilized or atomized universal plasma according to claim 1, further comprising an ultrafiltration step.

11. A process for the preparation of a lyophilized or atomized universal plasma according to claim 10, wherein the ultrafiltration step is combined with a dialysis step.

* * * * *